(12) United States Patent
Rosenman et al.

(10) Patent No.: US 9,011,373 B2
(45) Date of Patent: Apr. 21, 2015

(54) METHOD OF ACCESSING A CAROTID ARTERY OF A PATIENT

(71) Applicant: BioCardia, Inc., San Carlos, CA (US)

(72) Inventors: Daniel C. Rosenman, San Carlos, CA (US); Daniel Kayser, San Carlos, CA (US); Michael Keleher, San Carlos, CA (US); Nick Fravala, San Carlos, CA (US); Richard Cook, San Carlos, CA (US); Mark Tale, San Carlos, CA (US); Frank Arko, San Carlos, CA (US); Simon Stertzer, San Carlos, CA (US); Peter A. Altman, San Carlos, CA (US)

(73) Assignee: BioCardia, Inc., San Carlos, CA (US)

( * ) Notice: Subject to any disclaimer, the term of this patent is extended or adjusted under 35 U.S.C. 154(b) by 0 days.

(21) Appl. No.: 13/965,800

(22) Filed: Aug. 13, 2013

(65) Prior Publication Data
US 2013/0331932 A1 Dec. 12, 2013

Related U.S. Application Data

(60) Division of application No. 12/177,338, filed on Jul. 22, 2008, which is a continuation of application No. 11/016,448, filed on Dec. 17, 2004, now Pat. No. 7,402,151.

(51) Int. Cl.
*A61M 25/00* (2006.01)
*A61M 25/01* (2006.01)
*A61B 17/00* (2006.01)
(Continued)

(52) U.S. Cl.
CPC ............ *A61M 25/01* (2013.01); *A61M 25/0045* (2013.01); *A61M 25/0051* (2013.01); *A61M 25/0052* (2013.01); *A61M 25/0136* (2013.01); *A61M 25/0138* (2013.01); *A61M 25/0141* (2013.01); *A61M 25/0147* (2013.01); *A61M 25/0152* (2013.01); *A61M 2025/0687* (2013.01); *A61B 17/0057* (2013.01); *A61F 2/2427* (2013.01)

(58) Field of Classification Search
CPC ............. A61M 2025/0105; A61M 2025/0133; A61M 2025/015; A61M 2025/0161; A61M 25/0133; A61M 25/0136; A61M 25/0138; A61M 25/0141; A61M 25/0147; A61M 25/0152; A61M 2025/0147
USPC ............................ 604/95.01–95.04, 523–528
See application file for complete search history.

(56) References Cited

U.S. PATENT DOCUMENTS

| 5,329,923 A | 7/1994 | Lundquist |
| 6,027,863 A | 2/2000 | Donadio, III |

(Continued)

FOREIGN PATENT DOCUMENTS

EP 0667126 A1 8/1995

*Primary Examiner* — Matthew F Desanto
(74) *Attorney, Agent, or Firm* — K. David Crockett, Esq.; Crockett & Crockett, PC

(57) ABSTRACT

Methods for easy, atraumatic access to areas of the vasculature that are otherwise difficult to access, using steerable guide catheters constructed with components that are selected to provide optimal navigability, torque transfer, and push ability for a variety of typical percutaneous access routes. The catheter wall thickness in the deflecting segment of the guide catheter is about 1 French (⅓ mm) or less, and includes a slotted deflection tube, and this construction allows a very tight turning radius which in turn enables guide catheter access to regions of the vasculature that are otherwise inaccessible.

2 Claims, 9 Drawing Sheets

(51) Int. Cl.
*A61F 2/24* (2006.01)
*A61M 25/06* (2006.01)

(56) References Cited

U.S. PATENT DOCUMENTS

| | | | |
|---|---|---|---|
| 6,146,373 A | 11/2000 | Cragg et al. | |
| 6,251,092 B1* | 6/2001 | Qin et al. | 604/95.01 |
| 6,270,476 B1 | 8/2001 | Santoianni et al. | |
| 6,511,471 B2 | 1/2003 | Rosenman et al. | |
| 6,585,718 B2 | 7/2003 | Hayzelden et al. | |
| 7,381,198 B2* | 6/2008 | Noriega et al. | 604/95.04 |
| 7,402,151 B2* | 7/2008 | Rosenman et al. | 604/95.05 |
| 2003/0144657 A1* | 7/2003 | Bowe et al. | 606/41 |
| 2004/0044350 A1* | 3/2004 | Martin et al. | 606/139 |
| 2005/0043753 A1 | 2/2005 | Rabiner et al. | |
| 2005/0159774 A1* | 7/2005 | Belef | 606/200 |
| 2005/0267495 A1 | 12/2005 | Ginn et al. | |
| 2008/0021405 A1 | 1/2008 | Jacobsen et al. | |

\* cited by examiner

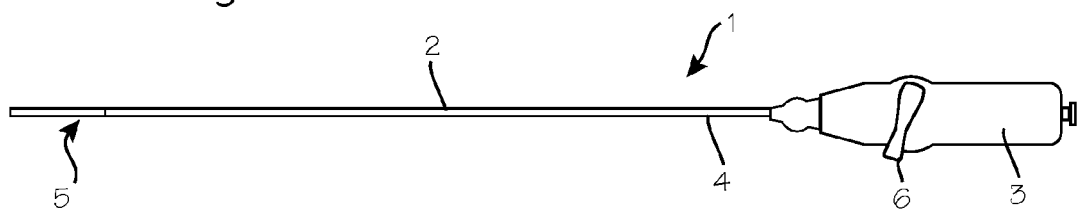
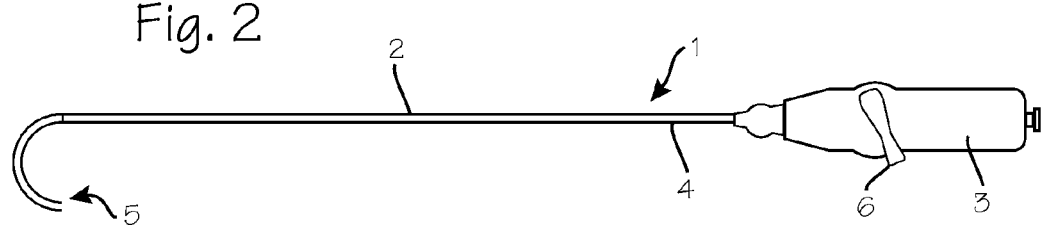
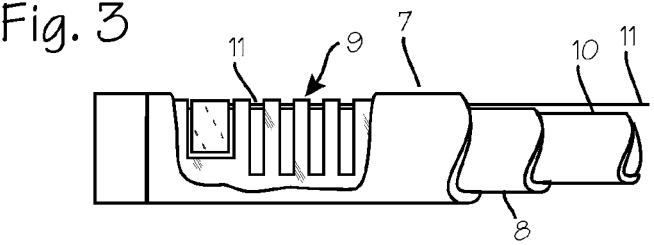
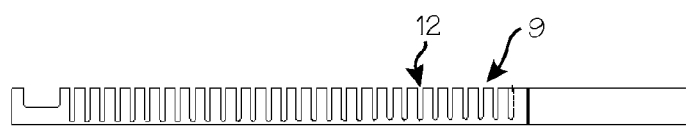

Fig. 7
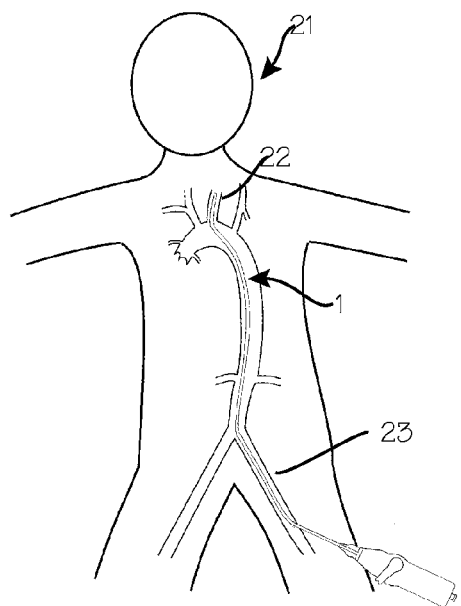
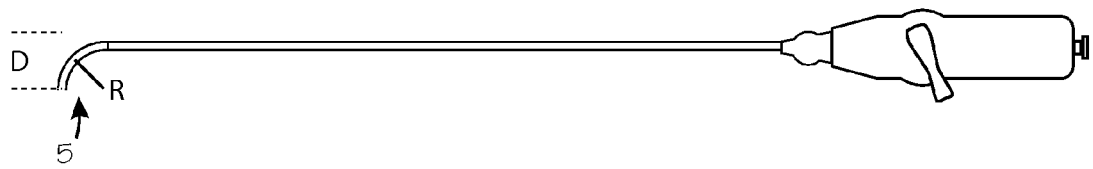
Fig. 7a

Fig. 8
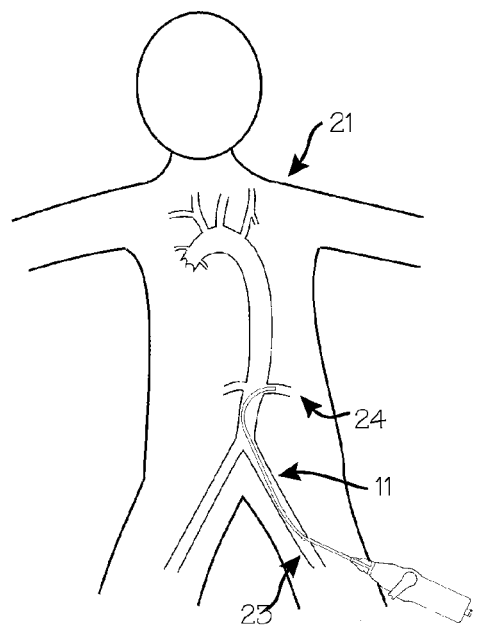
Fig. 8a

Fig. 10
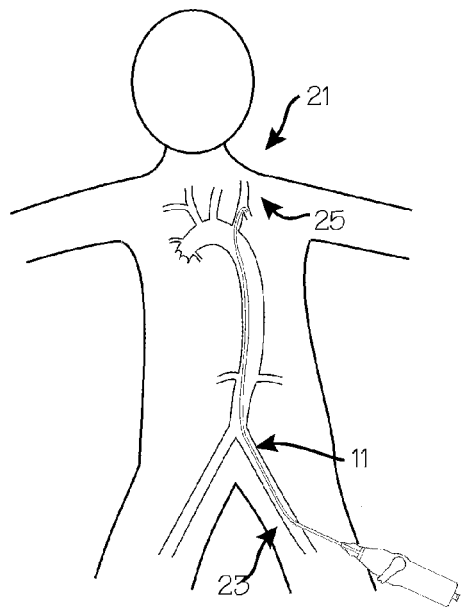
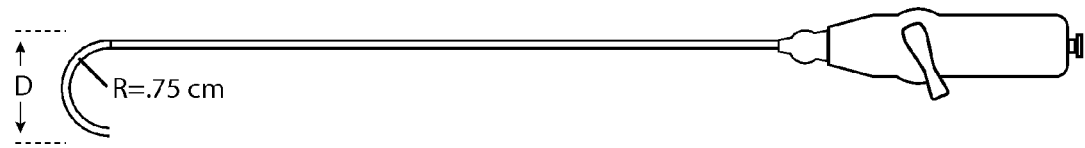
Fig. 10a 45-90°

Fig. 12
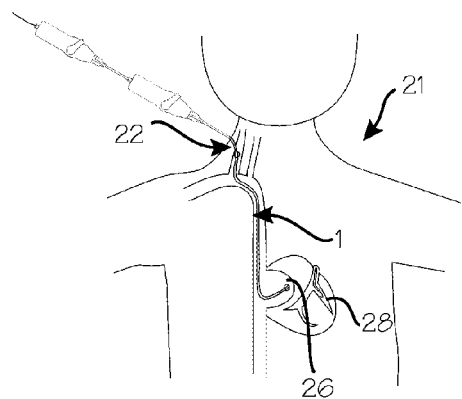
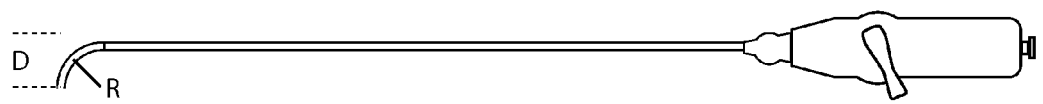
Fig. 12a

135°

METHOD OF ACCESSING A CAROTID ARTERY OF A PATIENT

This application is division of U.S. application Ser. No. 12/177,338, filed Jul. 22, 2008, which a continuation of U.S. application Ser. No. 11/016,448 filed Dec. 17, 2004 now U.S. Pat. No. 7,402,151.

FIELD OF THE INVENTIONS

The inventions described below relate the field of steerable guide catheters and sheaths.

BACKGROUND OF THE INVENTIONS

Guide catheters are used to gain access to the desired target location within the vasculature of a patient and provide a safe, smooth conduit to guide and support another device, such as an interventional catheter, to the target location. A guide catheter is typically inserted into the body through an introducer sheath and over a guidewire. Guidewires are long coiled wire structures that can be navigated through the vasculature and then used to lead another device through the vasculature. The guided device is typically the delivery device that carries an implant for deposit in the vasculature, an active device that carries out the diagnosis, therapy or intervention. Guide catheters can also be used to pass fluids for visualization, diagnosis or treatment.

A sheath is a type of guide catheter that also seals the entry point in the vascular space. The sealing is usually accomplished with a valve on the back of the sheath that either passively opens and closes when devices are inserted into it, or is opened and closed manually by the doctor when a device is inserted into it. The sheath protects the vessel from damage that might be caused by the guide or device that is passed within the sheath. Sheaths are typically thinner-walled and more flexible than guide catheters. They are typically straight-ended and may be inserted into the vessel over a guidewire or an introducer/obturator. An obturator/introducer is typically a long plastic tube with a distal tapered end that is longer than the device into which it fits and contains a central lumen to track over a guidewire. The obturator is usually flexible enough to allow the insertion of the device over it into a vessel or through a hemostatic valve and rigid enough to straighten out any pre-shaped guide that is over it.

Over the years, many guide catheters have been developed for treating specific diseases, delivering specific devices, or for accessing specific locations within the body. These guides are typically PTFE lined devices with walls made from a composite of thermoplastics and metal wire braid and coil reinforcements. They are thin-walled and flexible, but can transmit some torque from the proximal end to the distal end to allow the doctor to steer the distal end to the location of interest. Most guide catheters have a specific pre-formed shape that allows them to perform their narrow function and only their narrow function. They have been developed and customized over the years to reach one specific anatomic location only. The variety of achievable shapes is also limited because the guide must be inserted into the body in the straight configuration, so that the guide can be advanced to the location of interest without dragging or scraping along the vessel walls. Once at the desired location, the guide typically retakes its shaped configuration when the obturator or guidewire is removed from it. This flexibility detracts from the guide's ability to support interventional devices that are inserted through it. Also, the curvature of a pre-shaped guide must be limited, or it will not straighten out when the obturator is inside of it. These limitations of fixed shape guides point to a need for improved devices to enable atraumatic access to the target locations of interest.

A typical use of these devices is in interventional cardiology to treat a plaque build up or blockage in a patient's coronary artery. These blockages can lead to heart attacks and death. Typically, a patient presenting with symptoms is investigated with EKG tracings, a stress test or angiography (imaging with moving x-ray pictures and radiopaque fluids). In order to complete an angioplasty, the doctor would locate a femoral artery under the skin in the groin and install a sheath into an arterial opening, such as an 8 French sheath. The distal end of the sheath stays inserted into the artery and the proximal end, which has a hemostatic valve on it, remains outside the body. The surgeon would then insert a guide catheter that has a guidewire inside it through the sheath and into the femoral artery. Visualizing the devices on fluoroscopy, the surgeon manipulates the tip of the guide and guidewire retrograde up the aorta until he can engage the ostium of the coronary artery that has the suspected blockage in it. The surgeon then advances the guidewire into the artery toward the lesion of interest. After identifying the lesion location with angiography, the surgeon introduces an angioplasty balloon catheter into the guide (may or may not be over the guidewire inside the guide) and advances the angioplasty balloon to the lesion site. When correctly located, the surgeon inflates the balloon on the end of the angioplasty catheter to push the plaque back against the artery walls, thereby alleviating the blockage in the vessel. Once the procedure is completed, he removes the angioplasty catheter, guide, guidewire and sheath and disposes of them. The procedure for implanting a stent in the body is very similar to the previously described angioplasty procedure. After inflating a balloon to push the plaque against the wall of the vessel, the doctor inflates or expands a stent, which is left permanently behind in the vessel.

Interventional cardiologists now have procedures and different specifically shaped guides for the left and right coronary arteries, renal arteries, carotid arteries, internal mammary arteries, abdominal aorta, hepatic arteries and veins, pulmonary arteries, and veins, the atria and ventricles of the heart, mesenteric arteries, femoral arteries, neurological locations, and the coronary sinus of the heart. In many of the procedures, the fixed shape of the guide is not quite right for the patient anatomy and the surgeon must wrestle to get the guide into position, or discard the guide and try another shape. This consumes significant time in the catheterization lab which has costs today that run roughly $20 per minute. Although fixed guide catheters are relatively cheap medical devices today, the inability to access a target site in the body quickly due to anatomical variation or the propagation of disease can quickly cost hundreds of dollars. Extensive time in a fluoroscopy suite also exposes the physician and the patient unnecessarily high doses of radiation.

There are a small number of new guide catheters whose shape can be changed by the operator during surgery. These are called deflectable guide catheters. Their shape-changing ability allows them to be adjusted by the surgeon during a procedure to fit the anatomy of the patient, which normally varies due to disease, body type, genetics and other factors.

For example, Badger, Guiding Catheter With Controllable Distal Tip, U.S. Pat. No. 4,898,577 (Feb. 6, 1990) and Badger, Guiding Catheter With Controllable Distal Tip, U.S. Pat. No. 5,030,204 (Jul. 9, 1991) describe a steerable guide catheter with and outside diameter of 0.118" and an inside diameter of 0.078". A number of US, European and Japanese patents issued to Lundquist including U.S. Pat. Nos. 5,685,868, 5,228,441, 5,243,167, 5,322,064, 5,329,923, 5,334,145, 5,454,787, 5,477,856, 5,685,868, EP521595B1, JP 7255855A2, describe the use of slotted metal tubes such as nitinol torque tube elements in steerable catheters. Rosenman, Drug Delivery Catheters That Attach To Tissue And Methods For Their Use, U.S. Pat. No. 6,511,471 (Jan. 28, 2003) (the entirety of which is hereby incorporated by reference) describes a steerable guide catheter for delivering a medical device within the ventricle of the heart using the slotted Nitinol torque tube technology of Lundquist with a relatively large catheter lumen as it was used to pass other medical devices.

Qin, Deflectable Guiding Catheter, U.S. Pat. No. 6,251,092 (Jun. 26, 2001) describes a deflectable guide catheter whose deflection point is proximal from the distal tip. This patent does not enable a tight radius bending deflectable guide catheter that can track over a guidewire to locations of interest in the vascular tree in patients.

Farmholtz, Torqueable And Deflectable Medical Device Shaft, U.S. Pat. No. 6,716,207 (Apr. 6, 2004) describes a steerable catheter with slits in a tube component in the shaft. However, the bending point of this catheter is proximal of the end of the catheter, which results in a large sweep distance during bending, which is not desirable. Also, this catheter has a stiffer braided portion distal to the bending section, which decreases the trackability of the catheter. Also, this patent does not enable the construction of the shaft with a large central lumen or detail the cross sectional construction.

The ideal guide catheter is one that can adjust for varying patient anatomies while maintaining a thin wall and providing enough support for the devices passed through it to their target locations in the body. It should be smooth and lubricious on the inside and the outside surface. It should be stiff enough in torque to allow the doctor to direct the distal tip by manipulating the handle outside of the body. Minimizing the outside diameter of a guide catheter is important to minimize the size of the opening made in the patient's vessel to gain vascular access, and also to enable the distal portion of the device to be advanced through smaller vessels. Smaller openings are easier to close after the procedure and have less post-procedure healing complications. It is also important to have a large internal diameter in a device to allow easy passage of other interventional devices. The ideal guide catheter should be compatible with commonly used interventional guidewires, angioplasty balloon catheters, stent catheters and hemostatic introducer sheaths. The ideal catheter should also be visible on fluoroscopy and usable in an MRI suite.

SUMMARY

The devices and methods described below provide for easy, atraumatic access to areas of the vasculature that are otherwise difficult to access. The steerable guide catheters described below are constructed with components that are selected to provide optimal navigability, torque transfer, and push ability for a variety of typical percutaneous access routes. The steerable guide catheters enable percutaneous routes such as femoral artery approaches to the renal arteries, contralateral femoral artery, carotid arteries, and venous approaches to the fossa ovalis, the coronary sinus, etc. The catheter wall thickness in the deflecting segment of the guide catheter is about 1 French (⅓ mm) or less, and includes a slotted deflection tube, and this construction allows a very tight turning ratio which in turn enables guide catheter access to regions of the vasculature that are otherwise inaccessible. Furthermore, addition of the deflection capability distal to a preformed catheter shaft bend or proximal to a preformed catheter shaft may help optimize catheter shape and steerability for many interventional applications.

BRIEF DESCRIPTION OF THE DRAWINGS

FIG. 1 illustrates the deflectable guide catheter with the tip in its straight configuration.

FIG. 2 illustrates the deflectable guide catheter with the tip in its bent configuration.

FIG. 3 is a cutaway view of the distal end of the deflectable guide in FIG. 1.

FIG. 4 is a plan view of a nitinol deflection tube of the deflectable guide catheter

FIG. 7 is a schematic of a deflectable guide catheter in the body vasculature accessing a carotid artery from a femoral access site.

FIG. 7a illustrates the deflectable guide catheter adapted for accessing a carotid artery from a femoral access site.

FIG. 8 is a schematic of a deflectable guide catheter in the body vasculature accessing a renal artery from a femoral access site.

FIG. 8a illustrates the deflectable guide catheter adapted for accessing a renal artery from a femoral access site.

FIG. 10 is a schematic of a deflectable guide catheter in the body vasculature accessing the left internal mammary artery from a femoral access site.

FIG. 10a illustrates the deflectable guide catheter adapted for accessing the left internal mammary artery from a femoral access site.

FIG. 12 is a schematic of a deflectable guide sub-selecting a coronary vein from within another deflectable guide that is accessing the coronary sinus from a venous access site in the neck of a body.

FIG. 12a illustrates the deflectable guide catheter adapted for accessing a coronary vein from a venous access site in the neck of the body.

DETAILED DESCRIPTION OF THE INVENTIONS

Figure 5:
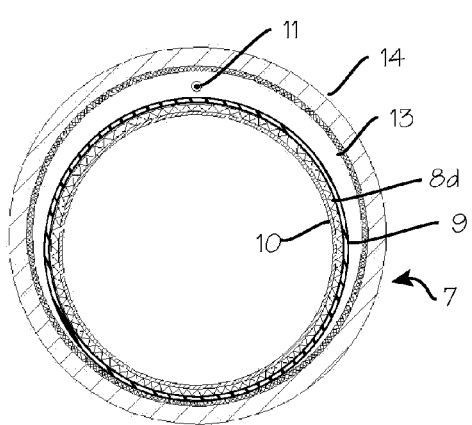
FIG. 5 is a cross section of the distal end of the tubing of the deflectable guide catheter shown in FIG. 1.

FIG. 1 illustrates the deflectable guide catheter with the tip in its straight configuration. The guide catheter 1 comprises a steerable guide catheter tube 2 with a catheter handle 3 mounted on the proximal end 4 of the guide catheter tube. The distal end of the guide catheter tube includes a deflectable segment 5 which is operated by a pullwire via manipulation of a steering lever 6 on the proximal handle. As illustrated in FIG. 2, the deflectable segment is bent in an arc as the steering lever turned by the operator.

FIG. 3 is a cutaway view of the distal end of the deflectable guide in FIG. 1. As shown in FIG. 3, the deflectable segment of the guide catheter tube 2 is comprised of an outer catheter shaft 7 and a catheter inner tube 8, with a deflection tube 9 sandwiched between the two. A PTFE liner 10 is disposed with in the catheter inner tube 8. That portion of the catheter inner tube 8 which resides inside the deflection tube (item 8d) comprises a coil covered with pebax. The portion of the catheter inner tube 8 which is proximal to the deflection tube (item 8p) comprises a braid covered with pebax or embedded with pebax. Its outer diameter is sized to slip fit within the inner diameter of the outer catheter shaft 7. A pullwire 11 runs between the inner catheter/deflection tube and the outer catheter shaft 7. A groove for receiving the pullwire may be cut in the outer wall of the inner tube or in the inner wall of the outer catheter shaft. The two shafts may then be melted, bonded, pull-truded, glued or welded to make a unitary tube with a central lumen and an eccentric pullwire lumen.

FIG. 4 is a plan view of a nitinol deflection tube of the deflectable guide catheter. The deflection tube 9 consists of a round stainless steel or nitinol tube with a specific pattern of slots 12 machined into it as shown in FIG. 4. The pattern of slots controls the shape that the distal portion of the catheter bends in and the sequence in which its sections bend. The slots 12 are cut to varying depths, widths and spacing to control the shape of the tube's bending. Slots may also include angular variations. Angular variations allow one to create flexibility in many directions, create three dimensional curve geometries, and create multiple deflecting segments in the same deflection component which can be controlled by separate pull wires which may used create curves in different planes from one another.

Figure 6:
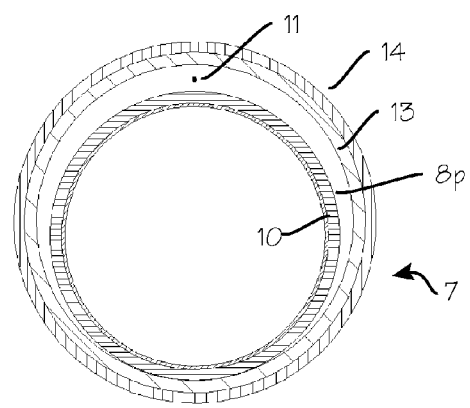
FIG. 6 is a cross section of the proximal portion of the tubing of the deflectable guide catheter shown in FIG. 1.

FIG. 5 is a cross section of the distal end of the tubing of the deflectable guide catheter shown in FIG. 1, illustrating the pebax covered coil 8, which may be reinforced with metal braid, immediately surrounding the PTFE liner 10 the deflection tube 9 immediately surrounding the catheter and catheter inner tube 8d and liner 10, and the catheter outer tube 7 with the pullwire 11 running between the deflection tube and the catheter inner tube 8d. The outer catheter shaft comprises a braided tube 13 covered in an outer jacket 14. FIG. 6 is a cross section of the proximal portion of the tubing of the deflectable guide catheter shown in FIG. 1, illustrating the PTFE liner 10, the catheter inner tube 8p immediately surrounding the liner (pebax and braid, which is roughly isodiametric with the covered coil), and the catheter outer tube 7 with the pullwire running between the deflection tube and the outer catheter shaft. The outer catheter shaft comprises a stainless steel braided tube 13 covered in the outer jacket 14 pebax. The basic structure of the steerable guide catheter may be modified as described below to enable an easily navigable guide catheter suited to access various target locations within the vasculature.

Carotid Artery Deflectable Guide/Guide-Sheath

FIG. 7 is a schematic of a deflectable guide catheter in the body vasculature accessing a carotid artery from a femoral access site, while FIG. 7a illustrates the deflectable guide catheter adapted for accessing a carotid artery from a femoral access site. The carotid artery is in the neck. It may be narrowed or occluded by plaque, which limits the amount of blood flowing to the brain. Doctors may want to intervene in the carotid artery to enlarge the lumen and increase the flow of blood to the brain. Carotid stenting is an important new interventional modality with the primary difficulty today being vascular access. As undue manipulation in such a procedure could dislodge plaque from the vessel with severe downstream repercussions of embolic stroke induced neurological deficit costing upwards of $50,000 per patient. With 140,000 carotid interventions estimated for 2006, there is an enormous need for a highly controllable thin walled deflectable guiding catheter to optimize access for this procedure as the primary goal today in carotid stenting is to minimize the catheter manipulations.

As shown in FIG. 7, which illustrates a patient 21 and the pertinent portion of the vasculature, including, for example, the left common carotid artery 22 which is accessed through an incision site in the groin in a femoral artery 23. Under fluoroscopic guidance, devices are threaded retrograde up the aorta, then antegrade down the left or right common carotid artery and possible down into the internal or external branches of the carotid arteries. To use a steerable guide-sheath 1, an interventionalist inserts a tapered obturator in the guide-sheath over a guidewire and inserts the tapered tip of the obturator into the femoral artery. The guide-sheath is then slid into the vessel over the obturator and flexible guidewire. (The obturator may be removed at this point or later.) Under fluoroscopic guidance, the interventionalist advances the guide-sheath to the carotid artery lesion region of interest. Once at the lesion site, the interventionalist withdraws the obturator but leaves the guide and guidewire in place, or the doctor removes the obturator and guidewire together, then reinserts the guidewire through the guide catheter. After confirming the lesion location and guide-sheath tip location under fluoroscopy or other imaging means, the doctor advances an interventional device through the sheath guide to start the intervention. The interventional device can be an atherectomy device to remove material, a balloon angioplasty device to push plaque back against the walls of the vessel, or a stent to hold the plaque back against the vessel walls and keep the vessel open. In some cases, an embolic protection device is deployed beyond the lesion before the angioplasty or stenting begins. The embolic protection device is typically a trap or net or filter that is placed downstream from the lesion. Interventional manipulations can cause pieces of plaque or calcium or thrombus to break off the lesion and proceed downstream due to the direction of the blood flow. In the carotid intervention, the downstream direction leads to the brain, where these emboli can lodge and cause strokes. The embolic protection devices are designed to trap these emboli and prevent them from entering the brain.

The deflectable guide catheter for carotid arteries should be a minimum of 6.25 (0.081") French internal diameter and less than an 8.25 (0.108") French outside diameter, leaving a 1 French wall thickness (thus permitting passage of 6F devices through the deflectable guide and permitting the deflectable guide through an 8F introducer). For some of the larger self-expanding nitinol stent systems, a version that is 7.25 French ID and 9.25 French OD may be applicable. It is ideally at least 90 centimeters total length. As shown in FIG. 7a, the deflectable segment 5 is deflectable from a straight position to a 90-degree bend in a sweep distance D (the sweep distance is the term we use for the maximum distance between the catheter main axis and the distal tip, which in this case is the same as the radius of curvature R) of a maximum of about 1 to 3 cm, preferably about 2.5 cm (1 inch). The distal tip of the deflectable carotid catheter consists of a soft tip that is atraumatic to any tissues it encounters. The carotid guide must have a smooth and lubricious interior to easily pass devices to the target lesion. The distal deflectable portion of the carotid guide should be stiff enough to support the interventional devices while they are being deployed in the carotid artery. The carotid deflectable guide shaft must be flexible enough in bending to track over a guidewire and obturator to reach the carotid artery from the femoral cutdown. The deflectable carotid sheath guide should be stiff enough in torque to allow the doctor to rotate the distal tip by rotating the proximal handle.

Each of these attributes is provided by the construction of the deflection segment. The construction of the catheter from the distal tip to the handle consists of a composite tube made up of several layers. The very distal tip of the tube consists of a soft tip of Pebax polymer (a polyether-based polyamide). The distal deflectable segment 5 consists of a PTFE liner that has an 0.083" inside diameter and a 0.001" wall thickness, a stainless steel coil with an inside diameter of 0.085" and a wire diameter of 0.001" impregnated with Pebax polymer (35D), a PTFE coated stainless steel pullwire with a 0.005" diameter, a slotted nitinol deflection tube with an inside diameter of 0.098" an outside diameter of 0.104" and a length of 1.25" and slots of varying width, spacing and depth to control its behavior in curing, and a soft and rubbery pebax distal outer cover (35D) with an inner diameter of 0.104" and an outer diameter of 0.108". The shaft proximal of the deflection area consists the same 0.001" thick PTFE liner, 1 over 2 stainless steel inner braid with a flat ribbon dimension of 0.004" wide by 0.001" tall, an eccentric dual lumen Pebax tube of various durometers, the stainless steel PTFE coated pullwire, a stainless steel outer braid and Pebax outer jacket of varying durometers whose outside diameter is 0.108" after tube construction. The lumen the pullwire travels in may be rotated around the axis of the shaft of the guide to even out the pull-wire length and moment of inertia of the tube with respect to the guide's main axis while the guide is being rotated by the user. The covered coil in the distal deflecting region of the catheter keeps the lumen round and open during the bending process. The slotted nitinol torque tube creates very tight bends when pulled on by the pull wire in a repeatable controllable manner. The slot pattern controls the radius of curvature (also sweep distance), the amount of curvature and the force required to curve the deflectable portion of the guide. The design of the slotted nitinol torque tube also controls the direction of bending of the distal end in a repeatable manner and provides the spring force to straighten the distal end of the catheter when the pullwire tension is released. The slotted nitinol torque tube allows these bending geometries while still transmitting torque from the handle to the distal end of the device and providing column support to devices inserted through the guide. The durometer of the inner and outer Pebax portions of the tube transition from a very soft distal outer cover (35D) for 1.5 inches to a soft Pebax (50D) for 2 inches at the distal end of the non-deflecting portion of the shaft to a harder Pebax (63D) segment for 5 inches to a harder Pebax segment (72D) for the rest of the shaft. These Pebax segments allow flexibility in bending for tracking around tight curves while providing enough column strength for the catheter to be advanced over the guidewire and support the force of the pullwire on the distal end of the catheter during deflection. The stainless steel braiding enhances the torque characteristics of the shaft and supports the column strength and resists buckling or kinking. The density of the braid in the braid layers and the thickness of the braid wires may be varied to adjust the bending, buckling, and torsional stiffness of the shaft at various sections but is generally between 25 and 100 picks per inch. The proximal shaft enters the molded plastic handle through an elastomeric strain relief. The pullwire exits the side of the shaft inside the handle and is affixed to a rotating crank. This rotating crank is joined to an external knob through one of the handle halves. The torque applied to the handle of the device is transmitted to the shaft of the device by a block that is constrained by the handles and is glued to the shaft inside the handles. The most proximal portion of the shaft is joined to a Pebax extension, a polycarbonate extension tube, and finally a luer which protrudes from the proximal portion of the handle. Attached to this luer is a hemostatic device that allows other devices to be placed through the guide without allowing blood under body pressure to escape. The hemostatic device has an infusion side arm to allow flushing of the sheath-guide while other devices are inserted within it.

To operate the device, the doctor actuates the knob to deflect the distal end of the tube in the same direction of the knob up to 90 degrees of bending. The components of the distal section of the tube keep the lumen of the device open and round during this deflection. The PTFE liner of the device enables other devices to slide though the catheter easily and smoothly.

Carotid stenting may be performed with this device from either a femoral artery access or a brachial artery access site in which the deflection must provide a 180° turn to go up to the carotid. In addition, for carotid access, two shapes with proximally located prefixed bends may also be desirable. In this situation, a thermoform bend is made such that the entire catheter in its undeflected shape appears like a VTECH catheter such that the distal 1.25 to 1.5 inches of the VTECH shape is the deflection component. Other proximal bends to the catheter, such as a deflection roughly 10 to 15 cm proximal to the distal tip in the opposite direction of the deflecting component (such that the distal end looks like an elongated "S") are also optional and easy to add once the deflection characteristics and shaft diameter requirements are defined.

Renal Artery Deflectable Guide/Guide-Sheath

FIG. 8 is a schematic of a deflectable guide catheter in the body vasculature accessing a renal artery from a femoral access site, while FIG. 8a illustrates the deflectable guide catheter adapted for accessing a renal artery from a femoral access site. It is estimated that 80,000 procedures involving renal artery access and stenting will be performed in the United States by 2007. A deflectable Guide/Guide sheath for renal stenting is a new solution that provides physicians with the ability to access difficult renal arteries with severe angulation. Such arteries are often only accessible with standard fixed guides from a brachial approach which has far more complications. Deflectable guides can provide back up support to advance wires and balloons and optimize their orientation into the center of the vessel lumen.

As shown in FIG. 8, which illustrates a patient 21 and the pertinent portion of the vasculature, including the renal artery 24 which is accessed through the vascular tree from an incision site in the groin in a femoral artery 23. The renal artery guide-sheath is ideally about 64 centimeters long. The guide-sheath is inserted in the femoral artery over a guidewire and obturator/introducer. The guide-sheath has a removable hemostatic valve on the proximal end to control hemostasis while other devices are put through it. It has an internal diameter of at least 6.25 French and an outside diameter of 8.25 French or less. The distal end of the renal guide-sheath should be able to bend in a curve of at least 135° from straight to access renal arteries that take off from the abdominal aorta at acute angles. The distal end of the sheath-guide must be stiff enough to support guidewires, balloon catheters and stents in the renal artery without losing its position in the ostium of the renal artery. As shown in FIG. 8a, the renal artery sheath guide should be capable of bending to the 135° angulation from straight within a sweep distance of 3 centimeters (about 1.25 inches). This allows the doctor to curve the distal end and access the renal artery in aortas that are narrow in diameter or calcified. The very distal tip of the renal artery guide-sheath should be soft and may be tapered on the outside diameter to allow deeper seating in the renal artery. The inside of the renal artery guide-sheath should be smooth and lubricious for the passage of guidewires, angioplasty balloons, balloon expanding and self-expanding stents. The renal artery guide-sheath should be stiff enough in torque to allow the doctor to get good one-to-one rotation correspondence between the handle and the distal tip for finding the renal artery. The distal tip of the guide-sheath is radiopaque so the doctor can see its location on fluoroscopy. The construction of the distal deflectable portion of the renal artery guide sheath consists of a PTFE liner, a Pebax infused stainless steel coil, a PTFE covered pullwire, a slotted nitinol deflectable member, and a Pebax outer jacket. The shaft proximal of the deflection tube consists of a PTFE liner, stainless steel braid, Pebax tube encasing a PTFE covered stainless steel pullwire, stainless steel braid, and Pebax outer jacket. The handle portion of the renal artery guide-sheath is the same as the carotid guide-sheath described above.

Abdominal Aortic Aneurysm Deflectable Guide

Figure 9:
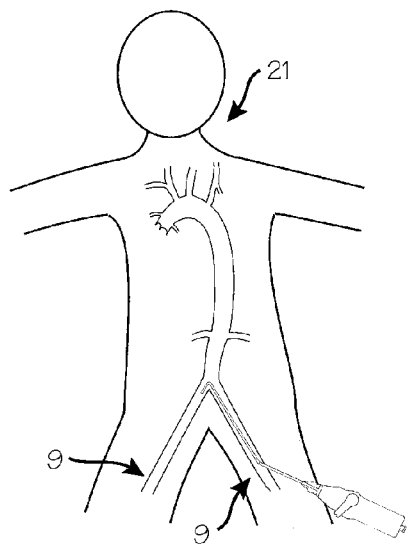
FIG. 9 is a schematic of a deflectable guide catheter in the body vasculature going from one side of the femoral aortic bifurcation to the other, around the horn.
Figure 9A:
FIG. 9a illustrates the deflectable guide catheter adapted for crossing the femoral aortic bifurcation.

FIG. 9 is a schematic of a deflectable guide catheter in the body vasculature going from one side of the femoral aortic bifurcation to the other, while FIG. 9a illustrates the deflectable guide catheter adapted for crossing the femoral aortic bifurcation. This procedure is used in abdominal aortic aneurysm stent procedures. An estimated 90,000 of these procedures will be performed in the United States in 2007.

As shown in FIG. 9, which illustrates a patient 21 and the pertinent portion of the vasculature, including the contralateral femoral artery 23R which is accessed through the vascular tree from an incision site in the groin in a left femoral artery 23L. In abdominal aortic aneurysm (AAA) graft stenting, the doctor inserts permanent implants into the abdominal aorta and femoral arteries of the legs. The abdominal aorta bifurcates into the two femoral arteries (right and left) in a "y" shape. Sometimes, the aorta is weakened and the vessel enlarges creating an aneurysm. The stent-graft is inserted by a catheter to cover the aneurysm area and prevent any further enlarging of the aneurysm. The graft typically consists of a nitinol and Dacron body with an aortic portion and a left and right leg portion that lie in the femoral arteries. During one part of the procedure to install the AAA stent grafts, the doctor needs to pass a guidewire from one femoral artery into the other, around the bifurcation of the femoral arteries. This involves making the guidewire turn 150° or more. For this application, a deflectable guide catheter with a minimum of 0.035" ID (0.9 mm or about 3 French) and an outside diameter of 6 French or less is desirable, although larger sizes such as would be used for renal stenting are also appropriate. What is necessary is that the guide be able to have a very tight turn at its distal end to redirect the guide wire down the other leg of the AAA graft. The guide should be a minimum of 35 centimeters long and a maximum of 90 centimeters long. As shown in FIG. 9a, the distal end of the guide catheter should bend up to 180° in a 1 cm radius. This allows the quick and easy passage of a guidewire from one femoral artery to the other and the connection of the AAA stent grafts. The distal shaft of the AAA guidewire passing guide consists of a PTFE liner with an ID of 0.055" and a wall thickness of 0.001", stainless steel coil with an ID of 0.058" and a 0.001" wire diameter embedded with Pebax polymer (35D, 0.001" wall thickness), a PTFE covered pullwire (0.0035" diameter), a slotted nitinol tube (0.070 ID, 0.076 OD, 1.25" length, 20 to 30 slots) to control the plane and shape of the bending, and a Pebax outer jacket (35D durometer, 0.076" ID, 0.078" OD). The very distal tip of the guide is a soft Pebax tip. The operation of the catheter is a follows. The shaft construction of this guide proximal to the deflectable portion consists of a the PTFE liner and a proximal composite shaft consisting of Pebax polymer, 1×2 stainless steel inner braid, the PTFE coated stainless steel pullwire, a 1×2 stainless steel outer braid, and a Pebax (72D) outer jacket. The handle of this device is the same as the previously described guide.

The doctor inserts the guide or guide-sheath into the femoral artery either over a guidewire or a guidewire and introducer/obturator. Under fluoroscopic or other guidance, the doctor advances the steerable guide up to the bifurcation and then actuates the knob on the handle. Rotating the knob on the handle pulls the pullwire which is attached to the crank in the handle and the distal end of the slotted deflection tube in the distal end of the catheter. The tension on the pullwire and the construction of the distal end of the catheter causes the distal end to curve in the tight radius toward the other leg of the bifurcation. The doctor can also torque the catheter by the handle to twist the distal curved end of the catheter in the abdominal aorta. Once the distal end of the catheter is pointed in the correct direction (down the other femoral artery), the doctor passes the guidewire up and over the bifurcation. He then snares the guidewire with a snare in the contralateral leg and pulls it out of the opening in the contralateral artery. This allows him to complete the installation of the stent graft. This application may be used with a two-part magnet wire in which magnetically attracted wires are advanced both through the steerable guide catheter and through the contralateral limb such that they are drawn to one another and no snaring of the wire is required. In such a situation one or two magnets can be used. If only one magnet is used on the tip of one wire, then the other wire would require ferromagnetic materials.

In other femoral artery interventions, doctors want to approach a lesion or occlusion and open it up with thrombolysis, angioplasty, atherectomy, stenting or a mechanical means of crossing the total occlusion followed by an angioplasty and stenting. Typically, these interventions take place in superior femoral arteries and are approached by the doctor through an arterial entry in the contralateral leg (side other than the leg with the blockage). In this procedure, the doctor inserts a guide-sheath into the vessel over a guidewire and dilator. The guide-sheath has a proximal hemostasis valve that allows the insertion and withdrawal of devices through its lumen, while preventing blood from escaping the arterial puncture (hemostasis). The doctor then uses the guide-sheath to move retrograde up the femoral artery to the bifurcation of the femoral arteries at the base of the abdominal aorta. Here, he deflects the tip of the guide-sheath to pass the guidewire around the bifurcation, which is a tight junction. He then follows the guidewire around the bifurcation with the guide-sheath to the location of interest in the opposite leg. There he completes the intervention with the guide-sheath providing support to the interventional devices as well as steering the guidewire and devices into specific sub-arteries off of the main femoral arteries. For this application, the inner diameter of the guide-sheath is 0.081" and the outside diameter is 0.107" and the length of the guide-sheath is between 60 and 90 centimeters (different versions). This same device has applications for placing coils in the hypogastric arteries or internal iliac arteries during AAA graft procedures, accessing and placing devices in the celiac trunk, and delivering devices into he superior mesenteric artery. Devices advanced into these vessels include guidewires, balloons, stents, infusion devices and fluids, devices for crossing occlusions with either blunt dissection or energy delivery, coils for obstructing blood flow, and thrombectomy catheter systems which are known in the field and developing.

Figure 9B:
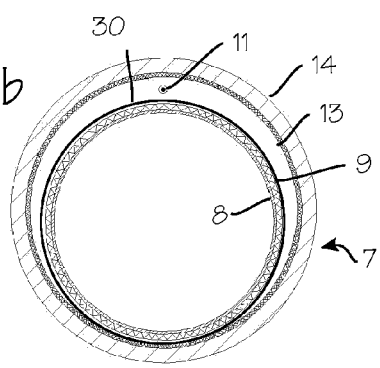
FIGS. 9b, 9c and 9d illustrate variations of the deflectable guide catheter adapted for crossing the femoral aortic bifurcation.
Figure 9C:
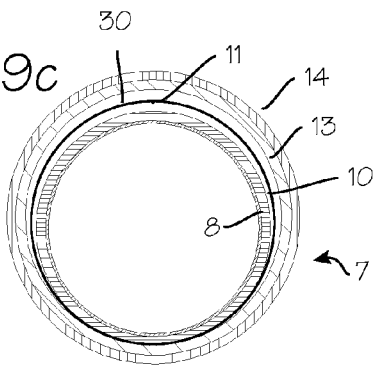
Figure 9D:
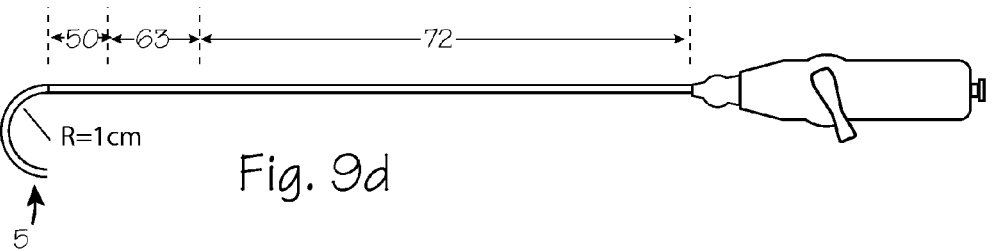

FIGS. 9b, 9c and 9d illustrate variations of the deflectable guide catheter adapted for crossing the femoral aortic bifurcation to support these procedures. The distal tip of the guide is a soft 35D Pebax soft tip. The composite shaft construction of the deflectable segment 5, just proximal to the distal tip, consists of a PTFE liner with an ID of 0.081" and a wall thickness of 0.001". Outside the liner is a stainless steel coil/35D Pebax composite with a round wire thickness of 0.001" and an outside diameter of 0.090" and a length of approximately 1.5 inches. A PTFE coated 0.0005" pullwire rides outside of the covered coil and is attached at the distal end to a c-ring which is glued to the covered coil and sits in a pocket in the slotted nitinol torque tube. The slotted nitinol torque tube has an inside diameter of 0.098", an outside diameter of 0.104" and a length of about 1.5 inches. The slotted nitinol torque tube is covered with a soft Pebax (35D) outer jacket 30 for its full length. The composite tubing construction proximal of the deflectable region consists of the PTFE liner, an inner stainless steel braid, a Pebax inner tubing (starting at 35D at the distal end and transitioning to 72D at the proximal end in segments), the PTFE-coated pullwire, an outer stainless steel braid, and an outer Pebax jacket that is fused through the outer braid. The distal segment of the outer jacket is a soft 35D durometer and the jacket transitions along the main body, segment by segment to a harder 72D durometer towards the proximal portion of the catheter shaft (such that segment 50 has a hardness of about 50D, segment 63 has a hardness of about 63D, and segment 72 has a hardness of 72D). Each segment of Pebax is butt-welded/heat fused to each adjoining segment to make one continuous smooth tube. The outer diameter of the fused composite tube is 0.108". The shaft of the catheter enters the handle through an elastomeric strain relief as previously described. The proximal end of the deflection pull wire is attached to a crank and knob in the handle as previously described. The most proximal portion of the handle is a female luer fitting as previously described. In this application, a hemostatic valve is attached to the proximal luer fitting to control the hemostasis during the procedure. The obturator for the Femoral Artery sheath guide is a hollow polyethylene shaft with a total length that is 4 centimeters longer than the guide-sheath with which it is used. The obturator has an internal diameter of 0.040" and an outside diameter of 0.065". The distal tip of the obturator tapers to an OD of 0.045" over 4 centimeters. The proximal end of the obturator has a female luer fitting on it.

Deflectable Guide for Left Internal Mammary Access

FIG. 10 is a schematic of a deflectable guide catheter in the body vasculature accessing the left internal mammary artery from a femoral access site, while FIG. 10a illustrates the deflectable guide catheter adapted for accessing the left internal mammary artery from a femoral access site. The left internal mammary artery is often used during coronary artery bypass grafting to bypass a blockage in one of the coronary arteries that feed the heart muscle. Over time, these bypass grafts themselves may become occluded with thrombus or atherosclerosis and are a target for an intervention, such as angioplasty, thrombolysis, or stenting. Gaining access to the ostium of the LIMA can be very difficult because of the angle it joins the left subclavian artery. If approached from the femoral artery access point, the guide must transverse up the aorta, into the left subclavian artery from the aorta and into the LIMA from the left subclavian artery. Although there are pre-shaped guides designed for this access, doctors still have difficulty accessing this region. Some doctors prefer to access the LIMA from the radial artery, because the approach can be straighter than from the femoral access, but the radial arteries are typically smaller than the femorals which can make inserting the sheath and guide catheter difficult.

As shown in FIG. 10, which illustrates a patient 21 and the pertinent portion of the vasculature, including the left internal mammary artery 25 which is accessed through the vascular tree from an incision site in the groin in a femoral artery 23. For this application, the LIMA guide is 90 centimeters long with an internal diameter of 4 French, an external diameter of 6.25 French, a 180-degree bend capability, and a sweep distance D of about 1.5 centimeters (a radius of curvature R of 0.75 cm), as shown in FIG. 10a. The guide must be supple enough to track over a guidewire to reach the LIMA ostium from the femoral approach. With the advent of new drug eluting stents a steerable guide which can pass 5 French stents (5.25F ID) and other devices and can be inserted through a 7F introducer (7.25F OD) are also of great value and readily realizable through this invention.

The construction of the deflectable left internal mammary artery guide is as follows. The distal tip of the guide is a soft 35D Pebax soft tip. The composite shaft construction proximal to the distal tip consists of a PTFE liner with an ID of 0.057" and a wall thickness of 0.001". Outside the liner is a stainless steel coil/35D Pebax composite with a round wire thickness of 0.001" and an outside diameter of 0.063" and a length of approximately 1.5 inches. A PTFE coated 0.0035" pullwire rides outside of the covered coil and is attached at the distal end to a c-ring which is glued to the covered coil and sits in a pocket in the slotted nitinol torque tube. (The guide wire attachment to the deflection tube is described in Rosenman, et al., Drug Delivery Catheters That Attach To Tissue And Methods For Their Use, U.S. Pat. No. 6,511,471 (Jan. 28, 2003), hereby incorporated by reference.) The slotted nitinol torque tube has an inside diameter of 0.070", an outside diameter of 0.075" and a length of ~1.5 inches. The slotted nitinol torque tube is covered with a soft Pebax (35D) outer jacket for its full length. The composite tubing construction proximal of the deflectable region consists of the PTFE liner, an inner stainless steel braid, a Pebax inner tubing (starting at 35D at the distal end and transitioning to 72D at the proximal end in segments), the PTFE-coated pullwire, an outer stainless steel braid, and an outer Pebax jacket that is fused through the outer braid. The distal segment of the outer jacket is a soft 35D durometer and the jacket transitions segment by segment to a harder 72D durometer towards the proximal portion of the catheter shaft. Each segment of Pebax is butt-welded/heat fused to each adjoining segment to make one continuous smooth tube. The outer diameter of the fused composite tube is 0.081". The shaft of the catheter enters the handle through an elastomeric strain relief as previously described. The proximal end of the deflection pull wire is attached to a crank and knob in the handle as previously described. The most proximal portion of the handle is a female luer fitting as previously described.

This device can be used as a guide-sheath by the addition of a hemostatic valve on the proximal end and the use of a tapered obturator during introduction in the artery as previously described. The ideal dimensions of the guide-sheath for this application are 0.056" ID with a 0.081" OD. The construction method of the guide sheath is the same as the previously described LIMA guide, but with the larger diameters.

An alternate embodiment of the deflectable LIMA guide includes a pre-shape to the portion just proximal of the deflectable end. This pre-shape makes it easier to thread the guide into the left subclavian vein. The pre-shaping is created by heating the catheter tube assembly in that shape for a period of time and cooling the device to room temperature. After cooling, the shaft retains the shape. The retaining method for heat treating the tube can either be an internal mandrel made of polymer or metal, or an external mold made of polymer, metal or glass.

Deflectable Guide-Sheath for Cardiac Venous Access

Figure 11:
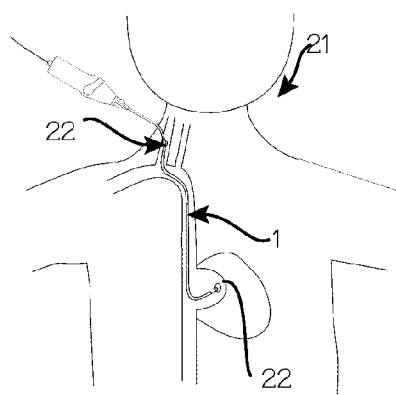
FIG. 11 is a schematic of a deflectable guide catheter in the body vasculature accessing the coronary sinus in the right atrium from a venous access site in the neck of the body.
Figure 11A:
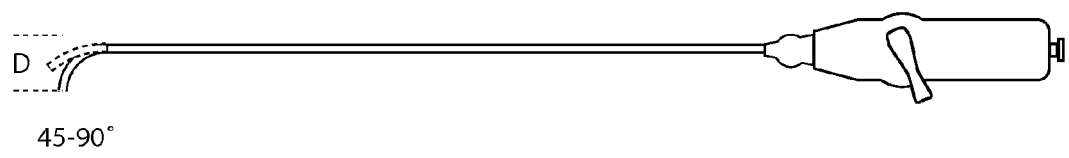
FIG. 11a illustrates the deflectable guide catheter adapted for accessing the coronary sinus in the right atrium from a venous access site in the neck of the body.

FIG. 11 is a schematic of a deflectable guide catheter in the body vasculature accessing the coronary sinus in the right atrium from a venous access site in the neck of the body, while FIG. 11a illustrates the deflectable guide catheter adapted for accessing the coronary sinus in the right atrium from a venous access site in the neck of the body. The coronary sinus is the ostium of the venous drainage from the heart into the right atrium. In some procedures, such as insertion of pacemaker wires or percutaneous valvuloplasty, or infusion of therapeutics to the heart tissue, the doctor desires to gain access to the heart's venous system through the coronary sinus. In the usual cases, this can be done quickly, but in a significant percentage of the cases, the coronary sinus is in an unusual or hard to reach position when accessed with pre-shaped guides. This is particularly true in patients whose hearts have undergone remodeling due to disease.

As shown in FIG. 11, which illustrates a patient 21 and the pertinent portion of the vasculature, including the coronary sinus 26 which is accessed through the vascular tree from an incision site in the jugular vein 27 of the patient. One preferred embodiment of a coronary sinus guide, shown in FIG. 11a, has a length of 60 centimeters, an internal diameter of 7.25 French, an external diameter of 9.25 French, a 45-90 degree of curvature, and a sweep distance D of 4 centimeters. This preferred embodiment also has a bend of 45° located about 10 centimeters proximal to the deflectable region. This bend orients the tip in the general direction of the normal coronary sinus. The deflectability of the tip allows for the doctor to adjust the shape of the guide to suit the specific patient anatomy.

A typical bi-ventricular pacemaker lead implantation procedure accessing the coronary sinus proceeds as follows. The doctor inserts the steerable guide catheter with a splittable sheath introducer already in place through a jugular vein in the neck of the patient over a guidewire or a guidewire and obturator. The doctor advances the steerable guide to the junction of the superior vena cava, inferior vena cava and right atrium of the heart. He steers and rotates the tip of the deflectable guide catheter and advances and retracts the guidewire from the tip in search of the coronary sinus. He may use radiopaque contrast and fluoroscopic guidance during this part of the procedure. Alternatively, he may use an electrode-tipped electrophysiology catheter inside the steerable guide catheter to look for the coronary sinus. The distinctive electrical patterns of the conduction in the coronary sinus and also along the right atrial wall above the cardiac conduction system (AV node and HIS bundle) compared to the atrial tissue will help guide placement and confirm entry to the doctor that the EP catheter is in the sinus. Once a guidewire is placed in the sinus, the doctor will advance it down to a specific branch of the coronary venous system that is appropriate to pace the left ventricle of the heart. He then removes the guide catheter leaving the splittable or peelable introducer in place and a pacemaker electrode is advanced through the splittable sheath to the location chosen over the guidewire.

The construction of the deflectable coronary sinus guide catheter is as follows. The distal tip of the guide is a soft 35D Pebax soft tip. The composite shaft construction proximal to the distal tip consists of a PTFE liner with an ID of 0.096" and a wall thickness of 0.001". Outside the liner is a stainless steel coil/35D Pebax composite with a round wire thickness of 0.001" and an outside diameter of 0.103" and a length of approximately 1.5 inches. A PTFE coated 0.006" pullwire rides outside of the covered coil and is attached at the distal end to a c-ring which is glued to the covered coil and sits in a pocket in the slotted nitinol torque tube. The slotted nitinol torque tube has an inside diameter of 0.101", an outside diameter of 0.117" and a length of about 1.5 inches. The slotted nitinol torque tube is covered with a soft Pebax (35D) outer jacket for its full length. The composite tubing construction proximal of the deflectable region consists of the PTFE liner, an inner stainless steel braid, a Pebax inner tubing, the PTFE-coated pullwire, an outer stainless steel braid, and an outer Pebax jacket that is fused through the outer braid. The durometer for both of the Pebax components in this shaft can be 72 D or slightly softer. The outer diameter of the fused composite tube is 0.121". The shaft of the catheter enters the handle through an elastomeric strain relief as previously described. The proximal end of the deflection pull wire is attached to a crank and knob in the handle as previously described. The most proximal portion of the handle is a female luer fitting as previously described. The pre-shaping of the distal portion of this catheter is achieved by a heat treatment of the composite shaft before final assembly as previously described.

An alternate embodiment of the deflectable coronary sinus guide is a straight (not pre-shaped catheter) that is pliable enough to conform to the patient anatomy.

An alternate embodiment of the deflectable coronary sinus guide includes softer Pebax distal segments so the guide can advance over a guidewire or electrophysiology catheter into the sinus and coronary venous tree.

An alternate embodiment of the deflectable coronary sinus guide would have an ID of more than 8 French and an OD of 10 French to allow an IS-1 connector on a pacemaker lead to fit through it (so the guide can be used until the lead is placed distally, then the guide can be threaded over the proximal portion of the lead, leaving the distal portion of the lead undisturbed in the heart).

Deflectable Guide for Cardiac Venous Sub-Selection

FIG. 12 is a schematic of a deflectable guide sub-selecting a coronary vein from within another deflectable guide that is accessing the coronary sinus from a venous access site in the neck of a body, while FIG. 12a illustrates the deflectable guide catheter adapted for accessing a coronary vein from a venous access site in the neck of the body, steering a guidewire or pacemaker lead into them. The coronary sinus leads retrograde to the great cardiac vein. The great cardiac vein is in communication with the middle and posterior cardiac veins of the heart. It is into these veins that the doctor wishes to position the left ventricular pacing lead. If he can place the pacing lead in a vein that is outside of the left ventricle, the left ventricle can be paced by the pacemaker. This makes the pumping of the paced heart much more effective. One way to place this lead is to use a cardiac venous subselector deflectable guide catheter to place a guidewire in the correct vein position.

As shown in FIG. 12, which illustrates a patient 21 and the pertinent portion of the vasculature, including the coronary sinus 26 and coronary veins 28 branching off the coronary sinus, which are accessed through the vascular tree from an incision site in the jugular vein 27 of the patient. The deflectable subselector guide catheter can be advanced through a sheath, a fixed shape guide, or through a deflectable coronary sinus guide catheter (or guide-sheath) as described above. The ideal cardiac vein deflectable subselector guide is 90 centimeters long, has an internal diameter of 0.052", an outside diameter of 0.076", a curvature of 90°, and a curve radius (sweep distance) of 1.0 cm. The cardiac vein deflectable subselector guide is flexible enough to track over a 0.018" or 0.035" guidewire. This flexible deflectable guide for venous sub-selection has a very small distal curve sweep and may be used once access to the coronary sinus is achieved. It may also be used with a length of protruding guidewire (about 3") to sweep the guidewire into the coronary sinus and then follow it into the coronary sinus. This has great advantages in that one less access device would be required.

The construction of the deflectable cardiac vein subselector guide catheter is as follows. The distal tip of the guide is a soft 35D Pebax soft tip. The composite shaft construction proximal to the distal tip consists of a PTFE liner with an ID of 0.052" and a wall thickness of 0.001". Outside the liner is a stainless steel coil/35D Pebax composite with a round wire thickness of 0.001" and an outside diameter of 0.055" and a length of approximately 1.5 inches. A PTFE coated 0.0035" pullwire rides outside of the covered coil and is attached at the distal end to a c-ring which is glued to the covered coil and sits in a pocket in the slotted nitinol torque tube. The slotted nitinol torque tube has an inside diameter of 0.065", an outside diameter of 0.070" and a length of about 1.5 inches. The slotted nitinol torque tube is covered with a soft Pebax (35D) outer jacket for its full length. The composite tubing construction proximal of the deflectable region consists of the PTFE liner, an inner stainless steel braid, a Pebax inner tubing (starting at 35D at the distal end and transitioning to 72D at the proximal end in segments), the PTFE-coated pullwire, an outer stainless steel braid, and an outer Pebax jacket that is fused through the outer braid. The distal segment of the outer jacket is a soft 35D durometer and the jacket transitions segment by segment to a harder 72D durometer towards the proximal portion of the catheter shaft. Each segment of Pebax is butt-welded/heat fused to each adjoining segment to make one continuous smooth tube. The outer diameter of the fused composite tube is 0.076". The shaft of the catheter enters the handle through an elastomeric strain relief as previously described. The proximal end of the deflection pull wire is attached to a crank and knob in the handle as previously described. The most proximal portion of the handle is a female luer fitting as previously described.

An alternate embodiment of the deflectable cardiac vein subselector guide consists of a inner PTFE liner, a layer of Pebax, a PTFE coated pullwire, an outer braid, and an outer jacket of Pebax fused through the outer braid. This construction has an even thinner wall and more flexible shaft than the previous embodiment. It tracks better over a guidewire but has slightly less torque transmission capability.

Deflectable Guide for Coronary Artery Use

Figure 13:
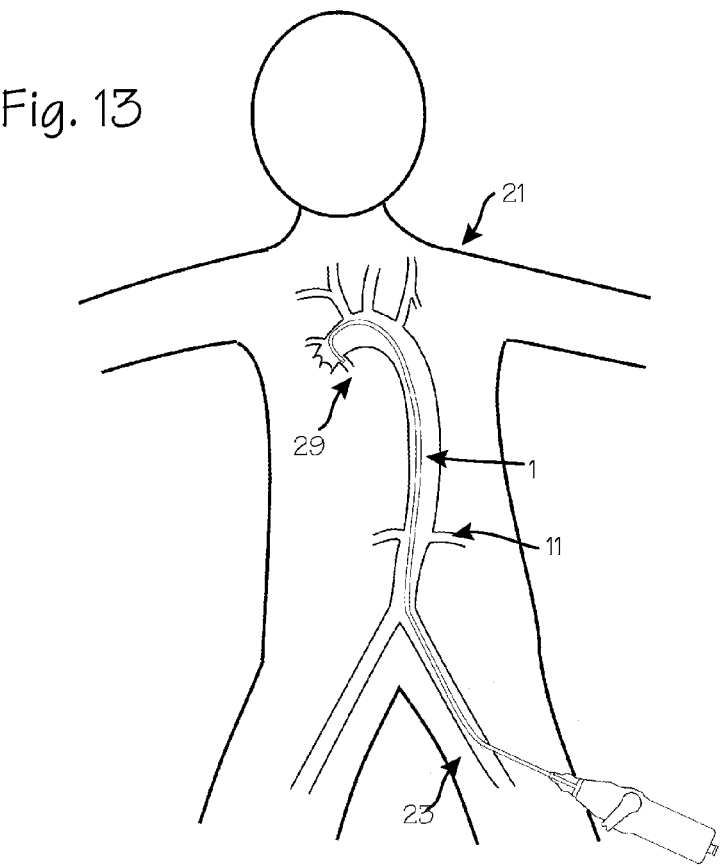
FIG. 13 is a schematic of a deflectable guide catheter in the body vasculature accessing the left coronary artery ostium in the aorta from a femoral arterial access site.
Figure 13A:
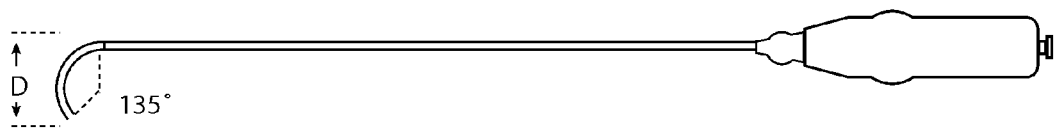
FIG. 13a illustrates the deflectable guide catheter adapted for accessing the left coronary artery ostium in the aorta from a femoral arterial access site.

FIG. 13 is a schematic of a deflectable guide catheter in the body vasculature accessing the left coronary artery ostium in the aorta from a femoral arterial access site, while FIG. 13a illustrates the deflectable guide catheter adapted for accessing the left coronary artery ostium in the aorta from a femoral arterial access site. The left coronary artery is one of the main blood vessels that feeds the heart muscle. Sometimes blockages develop in the left coronary artery or one of its subbranches.

As shown in FIG. 13, which illustrates a patient 21 and the pertinent portion of the vasculature, including the coronary artery 29 which is accessed through the vascular tree from an incision site in the groin in a femoral artery 23. Doctors typically access the coronary artery with a pre-shaped guide that is inserted into the femoral artery through a hemostatic sheath and advanced up the aorta over a guidewire or obturator until it reaches the aortic root. There it is manipulated until the guidewire and tip of the guide catheter can be lodged in the ostium of the coronary artery. Next the doctor performs an angiogram to visualize the lesion and then performs a balloon angioplasty or stenting to treat the lesions and open the target vessel. The origin of the left coronary artery is in the aortic root. The ideal left coronary artery deflectable guide catheter is 4.25 French ID, 6.25 French OD, 100 centimeters long, has a sweep distance of 3 centimeters, and can curve up to 135° from straight, as shown in FIG. 13a. Devices that are 5 French ID and 7 French OD may also be used in the coronary arteries.

The construction of the deflectable left coronary guide catheter is as follows. The distal tip of the guide is a soft 35D Pebax soft tip. The composite shaft construction proximal to the distal tip consists of a PTFE liner with an ID of 0.057" and a wall thickness of 0.001". Outside the liner is a stainless steel coil/35D Pebax composite with a round wire thickness of 0.001" and an outside diameter of 0.063" and a length of approximately 1.5 inches. A PTFE coated 0.0035" pullwire rides outside of the covered coil and is attached at the distal end to a c-ring which is glued to the covered coil and sits in a pocket in the slotted nitinol torque tube. The slotted nitinol torque tube has an inside diameter of 0.070", an outside diameter of 0.075" and a length of about 1.5 inches. The slotted nitinol torque tube is covered with a soft Pebax (35D) outer jacket for its full length. The composite tubing construction proximal of the deflectable region consists of the PTFE liner, an inner stainless steel braid, a Pebax inner tubing (starting at 35D at the distal end and transitioning to 72D at the proximal end in segments), the PTFE-coated pullwire, an outer stainless steel braid, and an outer Pebax jacket that is fused through the outer braid. The distal segment of the outer jacket is a soft 35D durometer and the jacket transitions segment by segment to a harder 72D durometer towards the proximal portion of the catheter shaft. Each segment of Pebax is butt-welded/heat fused to each adjoining segment to make one continuous smooth tube. The outer diameter of the fused composite tube is 0.081". The shaft of the catheter enters the handle through an elastomeric strain relief as previously described. The proximal end of the deflection pull wire is attached to a crank and knob in the handle as previously described. The most proximal portion of the handle is a female luer fitting as previously described. In this application, a hemostatic valve is attached to the proximal luer fitting to control the hemostasis during the procedure.

The deflectable left coronary artery guide can be converted to a guide-sheath by the addition of a tapered obturator and hemostatic valve. The obturator for the coronary artery guide-sheath is a hollow polyethylene shaft with a total length that is 4 centimeters longer than the guide-sheath it is used in The obturator has an internal diameter of 0.027" and an outside diameter of 0.052". The distal tip of the obturator tapers to an OD of 0.030" over 4 centimeters. The proximal end of the obturator has a female luer fitting on it. The hemostatic fitting for the coronary guide-sheath can have either a passive or active hemostatic valve. It can be supplied with a side arm to allow flushing of liquids around the inserted device if desired.

Deflectable Guide Sheath for Echographic Imaging Catheters

The deflectable guide catheter may also be adapted for use in steering an intracardiac echo device (ICE). Intracardiac echography is a new imaging method to look at devices in the heart with ultrasound energy. The ICE device has an ultrasound emitter and detector and recreates images from the echoes that bounce off the devices and tissues. Typically the ICE catheter is positioned on the right side of the heart from the femoral vein or the internal jugular vein. The ideal deflectable guide catheter for ICE guidance is 90 centimeters long, with an internal diameter of 10 French, and external diameter of 12 French, a degree of curvature of 90° and a sweep distance of 3 centimeters.

The construction of the deflectable guide for ICE catheters is similar to those described before with a liner, covered coil, deflection tube, PTFE coated pullwire, inner braid, Pebax polymer, outer braid and a Pebax outer jacket.

Deflectable Guide-Sheath for Neurological Interventions

The deflectable guide catheter can also be adapted for neurological interventions. A guide for neurological intervention must be small in outer diameter, thin-walled, flexible and still pushable and torqueable because the vessels in the brain are very small and tortuous. Neurological guides are typically inserted in the femoral artery or the neck and advanced to the brain. There they are used to conduct angiograms and to deploy devices such as coils or embolic particles to treat aneurysms or stroke. The preferred embodiment of the deflectable neurological guide catheter is 2 French internal diameter, 4 French external diameter, 124-centimeter length, with a distal deflectable region that can be curved to 135° through a sweep distance of 1 centimeter.

The construction of the deflectable neurological guide catheter is as follows. The distal shaft consists of a PTFE liner of inner diameter of 0.026" and a wall thickness of 0.001". A Pebax covered stainless steel coil of round wire diameter of 0.001" is attached to the liner. Outside the covered coil is a PTFE covered stainless steel pullwire with a diameter of 0.003". Outside of the stainless steel pullwire is a slotted nitinol deflection tube of inside diameter of 0.035" and an outside diameter of 0.039". The nitinol deflection tube is covered by a 35D Pebax outer jacket with an inside diameter of 0.040" and an outside diameter of 0.045". Proximal of the deflectable region, the shaft construction consists of the PTFE liner, Pebax polymer, a PTFE coated stainless steel pullwire, stainless steel braid, and a Pebax polymer outer jacket. The Pebax polymer transitions from a soft 30D durometer at the distal end to a hard 72D durometer at the proximal end in segments to allow bending and trackability while retaining pushability. The proximal end of the device is attached to a handle with a pullwire control knob as previously described.

Other applications of this thin walled steerable guide and sheath guide invention include transjugular intrahepatic portosystemic (TIPS) shunt placement, uterine fibroid biopsy and ablation, trans atrial septal delivery and manipulation of devices (for pulmonary vein ablation, implantation and or recovery of devices in the left atrial appendage and performing antegrade mitral and aortic valve manipulations and artificial valve implantation), and also for neurological access and delivery of coils and stents.

This is a fully scalable design platform. Devices with a one French wall are readily achievable in most configurations. Devices with inner diameters of 4.25 French that fit through 6 French Introducers, as well as larger devices with IDs of 6.25 French that fit through 8 French introducers and which are described here are of great value and enable all of these interventions which could not be performed before.

Further, with braiding and coiling in the primary catheter body, as well as the catheter deflection pull wire being selected from nonferromagenetic materials such as Titanium, MP35N, and Nitinol it is clear to one with knowledge in the art that all of these devices and applications could readily be developed to be compatible for performance under MRI imaging. The slotted nitinol torque tube technology applied in these designs is perfect for MRI applications with the elimination of these ferromagnetic materials and the incorporation of MRI contrast agents to enhance device imaging of the catheter body and distal deflectable torque tube cover polymer extrusions or in coatings.

Clearly for percutaneous valve implantation larger devices such as 16F to 30F would be desired. Such large devices may have applicability for the implantation of other large devices such as AAA grafts and present advantages for positioning prior to implant release.

Another application includes implantation of a self-expanding Nitinol device to close patent foramen ovale (PFO). Incidence of PFO in the general population is as high as 25% by some estimates. PFO is an anatomical inter-atrial communication with potential for right-to-left shunt linked to certain types of both stroke and migraine. A self-expanding PFO closure device, such as an AMPLATZER® PFO occluder, could be delivered percutaneously over a guidewire via femoral venipuncture and advancing the device to the foramen ovale for implantation. In addition to delivery of PFO closure devices, other cardiac procedures may be greatly facilitated with the guide catheter, including advancement of cardiac electrophysiology catheters for electrical mapping of the heart, pulmonary vein stent implantation, pulmonary vein ablation, mitral valve repair, percutaneous mitral valve implantation, aortic valve repair, and percutaneous aortic valve implantation.

By solving the problem of making a thin walled highly steerable guide catheter and deflectable guide sheath with valve and obturator, a whole new era of intervention has been enabled.

Thus, various embodiments of a guide catheter having a distally located deflectable segment with a wall thickness of 1 French or less, and with a distal end that can be curved in a tight radius of less than 1 to 2.5 cm, depending on the application, while maintaining an open lumen have been described. While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of accessing a carotid artery of a patient comprising the steps of:
    providing a deflectable guide catheter characterized by a distal end and a proximal end and a wall thickness, said deflectable guide catheter comprising a main body section and a deflectable segment disposed at the distal end thereof, said deflectable segment having a total wall thickness of about 1 French and an inner diameter of at least 6.25 French (0.08" or 2 mm) and comprising a deflectable member configured to provide a bend arc of about 90° and a sweep distance of about 1 to 3 cm, and a pullwire operably connected to the deflectable segment from the proximal end of the deflectable guide catheter;

inserting the deflectable guide catheter percutaneously, through an access point in a vasculature of the patient, and navigating the deflectable guide catheter through the vasculature to locate the deflectable segment into proximity with a carotid artery of the patient, and operating the deflectable segment and rotating the guide catheter as necessary to manipulate the deflecting segment into the carotid artery; wherein the deflectable segment consists of a PTFE liner, a coil disposed over the PTFE liner, the deflectable member, an outer jacket and the pullwire.

2. A method of accessing a carotid artery of a patient comprising the steps of:

providing a deflectable guide catheter characterized by a distal end and a proximal end and a wall thickness, said deflectable guide catheter comprising a main body section and a deflectable segment disposed at the distal end thereof, said deflectable segment having a total wall thickness of about 1 French and an inner diameter of at least 6.25 French (0.08" or 2 mm) and a pullwire operably connected to the deflectable segment from the proximal end of the deflectable guide catheter;

inserting the deflectable guide catheter percutaneously, through an access point in a vasculature of the patient, and navigating the deflectable guide catheter through the vasculature to locate the deflectable segment into proximity with a carotid artery of the patient, and operating the deflectable segment and rotating the guide catheter as necessary to manipulate the deflecting segment into the carotid artery; wherein the deflectable segment consists of a PTFE liner, a coil, a deflectable member, the pullwire and an outer jacket, with said coil disposed over the PTFE liner.

* * * * *